(12) United States Patent
D'Amico

(10) Patent No.: US 8,119,072 B2
(45) Date of Patent: Feb. 21, 2012

(54) DISPOSABLE AIR FRESHENER INCLUDING GEL OR POLYMER FRAGRANCE SUPPORT

(75) Inventor: Daniel D'Amico, South Salem, NY (US)

(73) Assignee: Scent2Market Inc., Yonkers, NY (US)

( * ) Notice: Subject to any disclaimer, the term of this patent is extended or adjusted under 35 U.S.C. 154(b) by 621 days.

(21) Appl. No.: 12/126,510

(22) Filed: May 23, 2008

(65) Prior Publication Data
US 2008/0292509 A1    Nov. 27, 2008

Related U.S. Application Data

(60) Provisional application No. 60/931,358, filed on May 23, 2007.

(51) Int. Cl.
*A62B 7/08* (2006.01)
(52) U.S. Cl. ....................................................... 422/126
(58) Field of Classification Search .................. 422/126
See application file for complete search history.

(56) References Cited

U.S. PATENT DOCUMENTS

| | | | |
|---|---|---|---|
| 3,558,055 A | 1/1971 | Storchheim | |
| 4,482,799 A | 11/1984 | Pricenski et al. | |
| 4,610,694 A | 9/1986 | Krusche | |
| 4,666,638 A | 5/1987 | Baker et al. | |
| 4,748,313 A | 5/1988 | de Rudnay | |
| 5,019,434 A | 5/1991 | Matsumoto | |
| 5,057,903 A | 10/1991 | Olla | |
| 5,574,821 A | 11/1996 | Babasade | |
| 5,577,156 A | 11/1996 | Costello | |
| 5,647,052 A | 7/1997 | Patel et al. | |
| 5,796,914 A | 8/1998 | Gatzemeyer et al. | |
| 5,840,246 A * | 11/1998 | Hammons et al. | 422/4 |
| 5,903,710 A | 5/1999 | Wefler et al. | |
| 5,976,503 A | 11/1999 | Martin et al. | |
| 6,039,212 A | 3/2000 | Singh | |
| 6,085,026 A | 7/2000 | Hammons et al. | |
| 6,349,168 B1 | 2/2002 | Jaworski | |
| 6,381,408 B1 | 4/2002 | Jaworski et al. | |
| 6,390,453 B1 | 5/2002 | Frederickson et al. | |
| 6,542,217 B2 | 4/2003 | Boyd et al. | |
| 6,551,560 B1 * | 4/2003 | Flashinski et al. | 422/125 |
| 6,652,606 B1 | 11/2003 | Zimmerman | |
| 6,737,025 B2 | 5/2004 | Boyd et al. | |

(Continued)

FOREIGN PATENT DOCUMENTS
EP    1240907 A1    9/2002
(Continued)

OTHER PUBLICATIONS
International Search Report dated Dec. 1, 2008.
(Continued)

*Primary Examiner* — Walter D Griffin
*Assistant Examiner* — Christopher Vandeusen
(74) *Attorney, Agent, or Firm* — Buchanan Ingersoll & Rooney PC

(57) ABSTRACT

Embodiments of the invention provide a fragrance distribution device comprising an electrical resistor, a plug or other power source, and a fragrance in a polymer or thermoplastic carrier. The polymer or thermoplastic carrier may include, for example, metal inclusions, which may be powdered metal. These metal inclusions are believed to enhance heat distribution throughout the carrier, thus allowing a more uniform and reliable release of fragrance.

12 Claims, 4 Drawing Sheets

U.S. PATENT DOCUMENTS

| | | |
|---|---|---|
| 6,969,008 B2 | 11/2005 | Helf et al. |
| 7,095,953 B2 | 8/2006 | Caserta et al. |
| 7,137,570 B2 | 11/2006 | Wheatley et al. |
| 7,227,108 B2 | 6/2007 | Clothier et al. |
| 7,293,719 B2 | 11/2007 | Wheatley et al. |
| 2002/0076214 A1 | 6/2002 | Vieira |
| 2002/0079365 A1 | 6/2002 | Boyd et al. |
| 2002/0080330 A1 | 6/2002 | Boyd et al. |
| 2002/0081229 A1 | 6/2002 | Boyd et al. |
| 2004/0251414 A1* | 12/2004 | Rodewald ............ 250/339.07 |
| 2005/0011883 A1 | 1/2005 | Clothier et al. |
| 2005/0096220 A1 | 5/2005 | Tepper et al. |
| 2005/0184059 A1 | 8/2005 | Clothier et al. |
| 2006/0198768 A1* | 9/2006 | Gupte et al. ............ 422/125 |
| 2007/0131676 A1 | 6/2007 | Clothier et al. |

FOREIGN PATENT DOCUMENTS

| | | |
|---|---|---|
| GB | 2421436 A | 6/2006 |
| WO | 01/68154 A1 | 9/2001 |
| WO | 0193919 A1 | 12/2001 |
| WO | 03/077962 A2 | 9/2003 |
| WO | 2004020004 A1 | 3/2004 |

OTHER PUBLICATIONS

Supplementary European Search Report for EP Application No. 08 78 0695 dated Feb. 25, 2011.

* cited by examiner

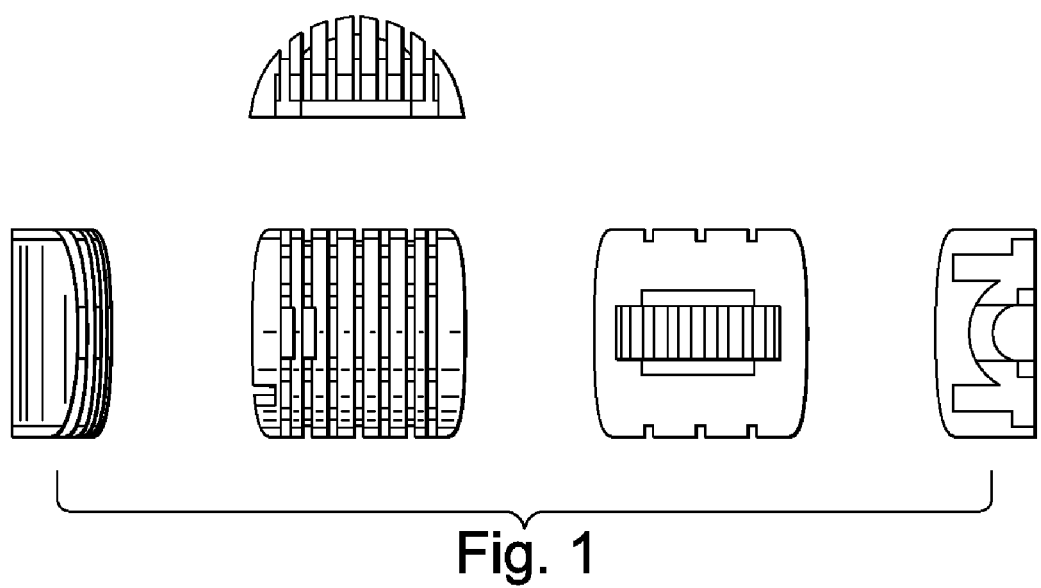
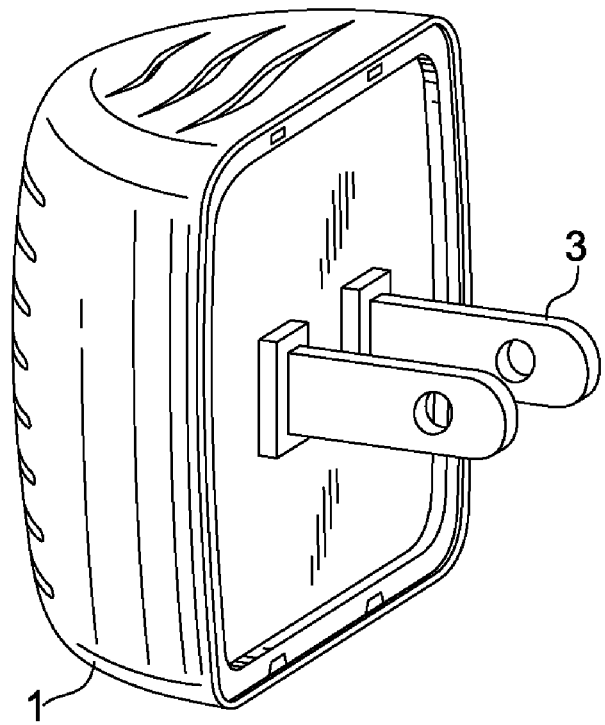
Fig. 1
Fig. 2

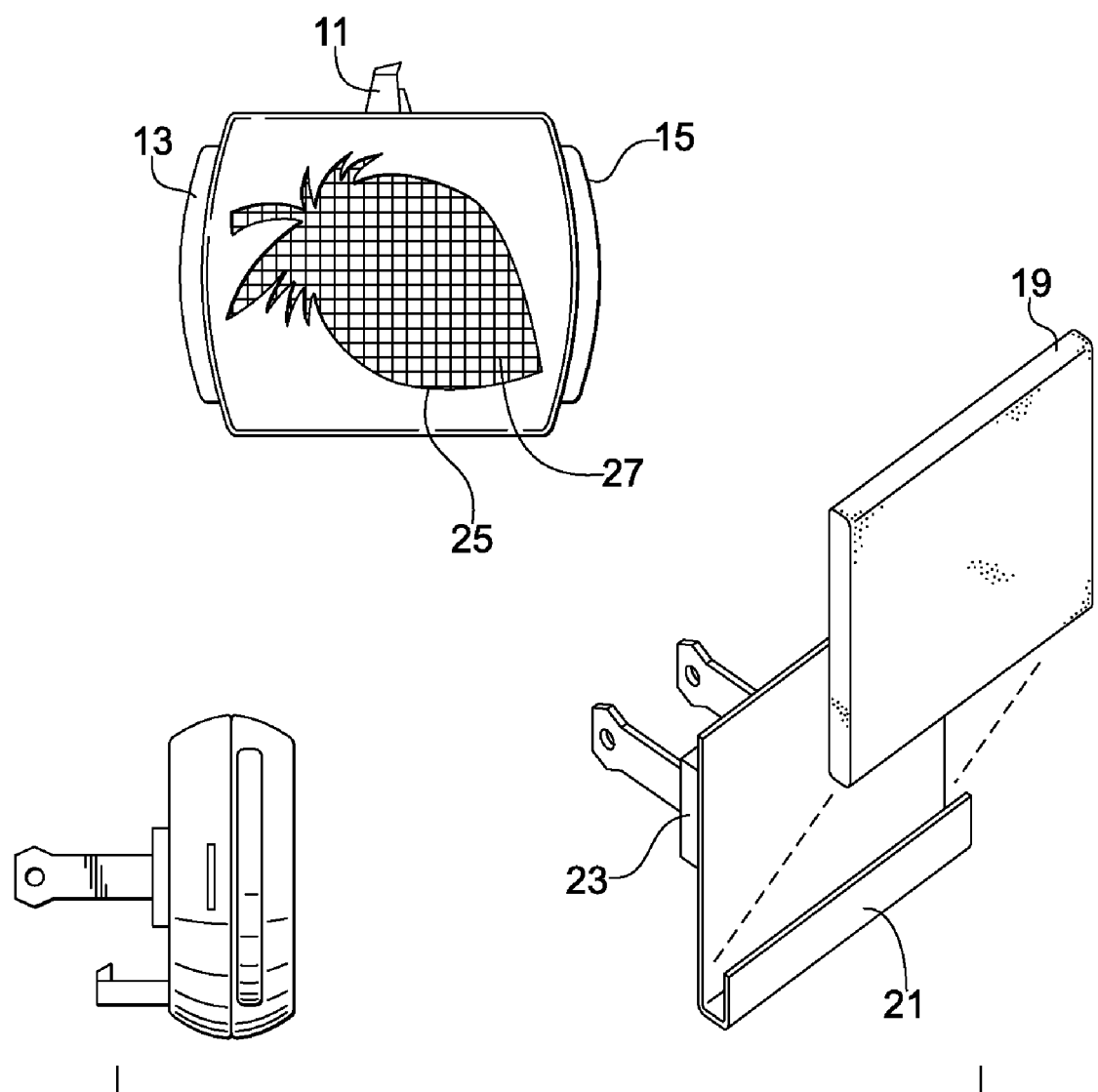

DISPOSABLE AIR FRESHENER INCLUDING GEL OR POLYMER FRAGRANCE SUPPORT

CLAIM TO PRIORITY

This application claims priority to U.S. Provisional Patent Application No. 60/931,358, filed on May 23, 2007, and having common inventor. That application, including all figures and drawings, is incorporated by reference as if fully rewritten herein.

BACKGROUND OF THE INVENTION

1. Field of the Invention

The invention relates to the fields of scent and aroma management. This may include, for example but not be limited to increasing the amount of desirable volatile organic compound (for example, fragrances) in a room or other area.

2. Background of the Art

Many devices for providing a fragrance to an area over a period of time are known. Generally, these devices operate by allowing a fragrance contained in the device to diffuse from the device and into the atmosphere. Diffusion of fragrance may be enhanced, for example, by heating the fragrance, by including the fragrance in a volatile carrier, or by a combination of those. Diffusion of fragrances and their general intensity is governed by their equilibrium vapor pressure. Fragrances with a high equilibrium vapor pressure have a high volatility and quickly evaporate.

The useful lifespan of a fragrance device is limited by the amount of fragrance that is able to be distributed from the device. After the fragrance supply of the device is exhausted, either the device is replaced in its entirety, or the fragrance is replaced. This latter may be done, for example, by replacement of a removable cartridge in the fragrance device.

Known devices for fragrance distribution may present a number of heretofore unresolved challenges. For example, selection of a carrier that allows uniform distribution of the fragrance at a selected rate is difficult. Some carriers and fragrances evaporate too quickly. This results in an undesirably short lifespan for the fragrance distribution product and potentially an undesirably intense aroma.

Other carriers and fragrances may diffuse too slowly, or diffuse to an extent insufficient to create the desired fragrance in a room of large size. This could result in a fragrance concentration that is too low to be effective for an intended use.

Use of heat to aid in the distribution of carrier from a fragrance has been tried in the past. Unfortunately, many heat assisted fragrance distributors share problems with their non-heated counterparts. For example, fragrance may diffuse too rapidly when the carrier is heated. Because the application of heat is often not uniform across the entirety of a fragrance diffuser (for example, when the heat is applied to only one side or to the bottom of a container holding the fragrance and carrier), the fragrance may not be uniformly released from the carrier.

This is particularly troublesome in applications where the carrier is a solid carrier, and where there is no opportunity for the carrier to be placed in contact with the heating element. This can result in low fragrance capacity (because only a small amount of carrier is provided) or in significant wasted fragrance and carrier (because more carrier is provided than can be placed in contact with or operatively close to the heat source.

It would be desirable to have a fragrance distribution device that is able to distribute heat uniformly or near-uniformly about the entirety of the carrier. It would further be desirable to have a fragrance distribution device that provides a more uniform and/or more controllable distribution of fragrance.

BRIEF SUMMARY OF THE INVENTION

Embodiments of the invention provide a fragrance distribution device comprising an electrical resistor, a plug or other power source, and a fragrance in a polymer or thermoplastic carrier. The polymer or thermoplastic carrier may include, for example, metal inclusions, which may be powdered metal. These metal inclusions are believed to enhance heat distribution throughout the carrier, thus allowing a more uniform and reliable release of fragrance.

A further embodiment of the invention provides a fragrance retained in a polymer or thermoplastic carrier. Metal is distributed throughout the carrier and believed to enhance heat distribution when the carrier is subjected to heat.

Methods of providing a fragrance by using one or more of the above structures are also included herein.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings:

FIG. 1 shows multiple views of a solid reservoir (interchangeably called a fragrance support herein) of one embodiment of the invention.

FIG. 2 shows a solid reservoir of the invention contained within a fragrance distribution device of the invention. The cover may be held in place, for example, by a snap fit or other adhesive.

FIG. 6 shows a further embodiment of the invention.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Embodiments of the invention provide a gel or polymer fragrance carrier including a fragrance and one or more other additives. In particularly preferred embodiments of the invention, another additive is metal inclusions, preferably powdered aluminum.

Figure 3:
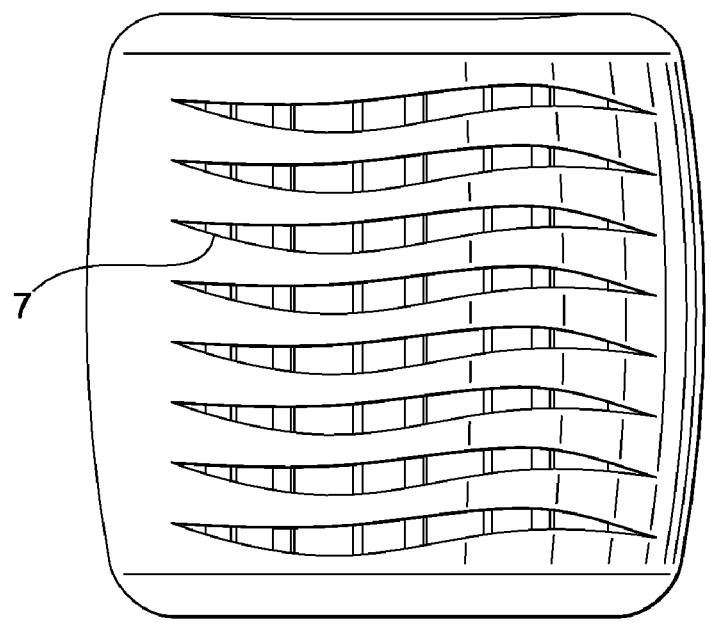
FIG. 3 shows a front view of a fragrance distribution device of an embodiment of the invention.
Figure 4:
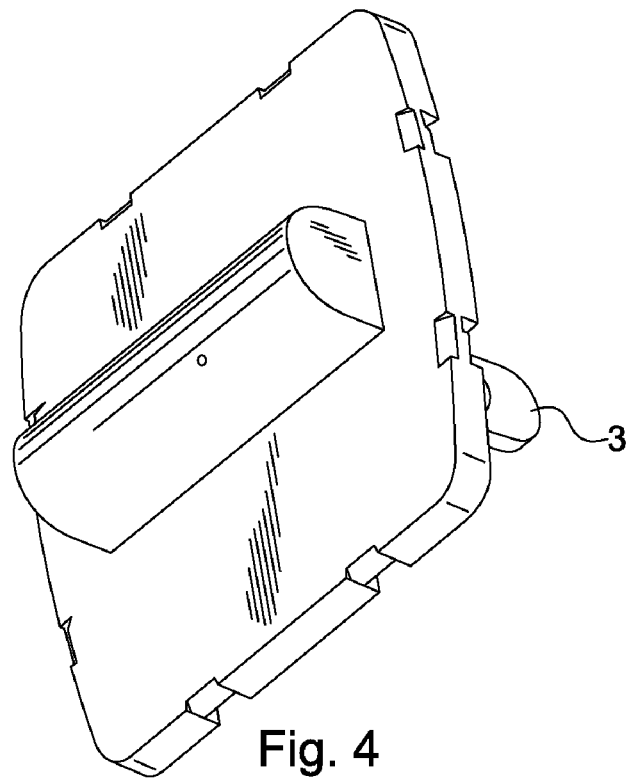
FIG. 4 shows a resistor with plug. The resistor is covered by plastic, which may have holes in the plastic to allow heat transfer.

Multiple views of a fragrance reservoir useful in one embodiment of the invention are shown in FIG. 1. Such a fragrance reservoir may be enclosed within a fragrance dispensing device and/or may be molded directly to a resistor. The embodiment in FIG. 2 shows a cover 1 and a plug/resistor 3, which is optionally coated in plastic. FIG. 3 shows a further embodiment of the invention. Optional vents 7 and are also included in this embodiment. FIG. 4 shows a resistor with a conventional plug for electricity. The fragrance reservoir may be designed to fit snugly over the resistor. Such a design is shown in FIG. 1.

Figure 5:
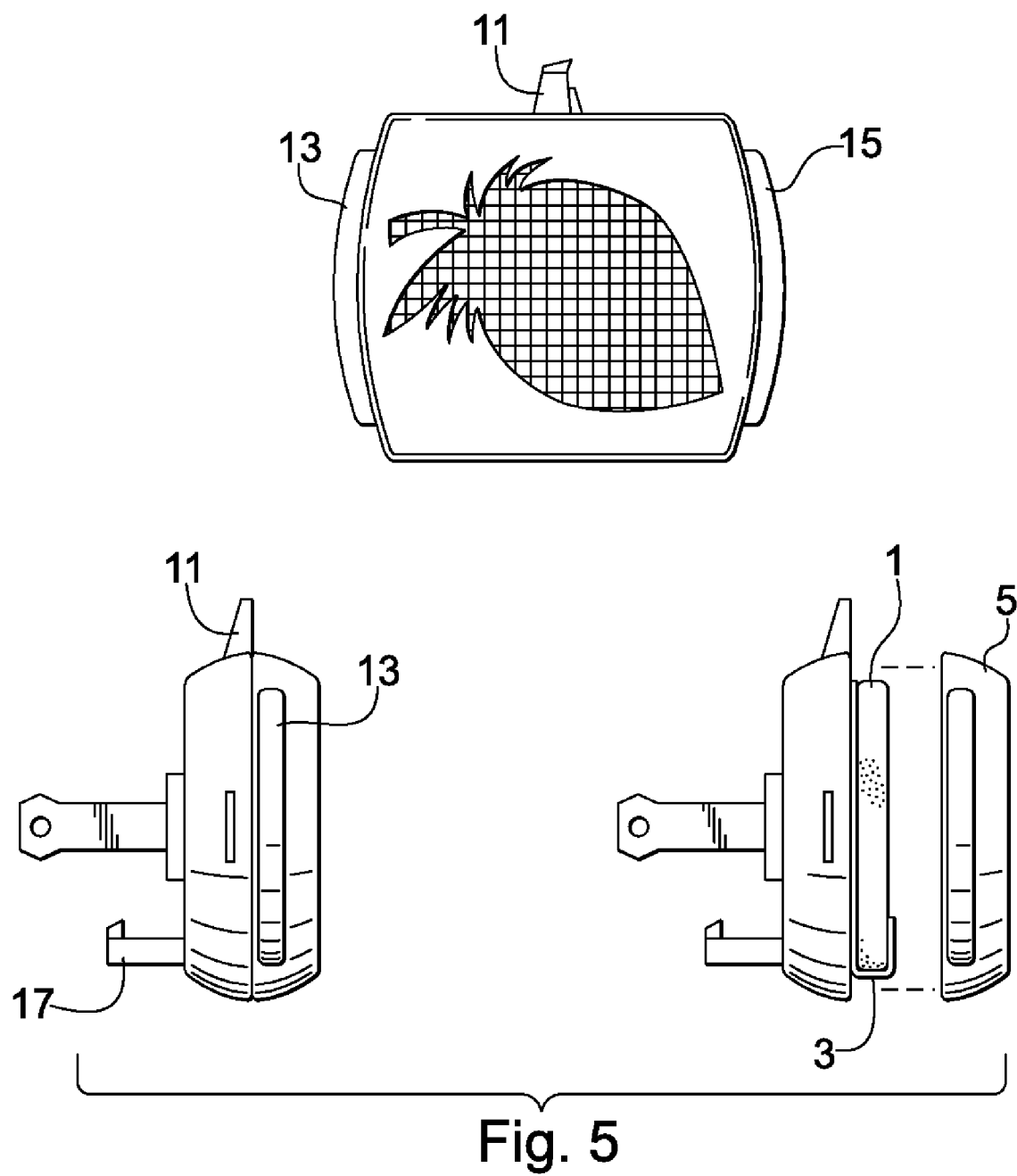
FIG. 5 shows an additional embodiment of the invention. It includes an optionally screened design on the cap.

FIG. 5 shows an additional embodiment of the invention, including an optional "child-safe" feature. In this embodiment of the invention, top release button 11 and side release buttons 13 and 15 must be depressed to remove the air freshener from a standard wall outlet after the safety tab 17 has engaged. FIG. 5 also shows the fragranced polymer 1, heat sink/plug combination 3 and cover 5 shown in FIG. 1. Although buttons 13 and 15 server as a release mechanism in this embodiment, in another embodiment they may be immobile and serve as grips for easy removal of the air freshener from an outlet.

FIG. 6 shows an embodiment of the invention including a disposable, replaceable fragranced polymer 19 that is placed in a resistor/plug tray 21. This tray is then inserted in a housing 23 that may optionally include safety releases 11, 13, and 15. The embodiment shown in FIG. 6 also includes a cutout 25 with a screen 27 allowing release of the fragrance.

Polymer Carriers

Embodiments of the invention include the fragrances in a polymeric carrier, which also may be referred to herein as a reservoir. One preferred polymeric carrier is polyethylene vinyl acetate (EVA). EVA is a copolymer of ethylene and vinyl acetate. The EVA has no odor by its nature, however, it can adsorb or otherwise be permeated with a fragrance. EVA approaches elastomeric materials in softness and flexibility, yet can be processed like thermoplastics. EVA is also moderately effective in the distribution of heat necessary to provide an approximately uniform heating effect throughout the polymeric carrier.

EVA used in the invention may have a molecular weight in the range of, for example, 10,000 Daltons to 100,000 Daltons, more preferably 22,000 to 87,000 Daltons. Fragrance may be introduced into the polymer at weight percents varying from 10 to 90%, from 20 to 80% from 30 to 70%, from 30 to 60%, and from 30 to 50%. In further embodiments, fragrance is introduced into the polymer at a weight percent of about 1%, about 10%, about 20%, about 30%, about 40%, about 50%, about 60%, about 70%, about 80%, about 90%, or about 95%.

Other elastomeric or thermoplastic carriers or combinations thereof may be used as carriers, so long as they will release fragrance upon heating. Other suitable polymeric materials share the beneficial properties of EVA and may be substituted for use in embodiments of the invention. These include, for example, but are not limited to ethyl vinyl alcohol, high density polyethylene, low density polyethylene, polystyrene, acrylic polymers, polycarbonates, polyurethanes, nylons, and mixtures and copolymers of the foregoing.

Gellants may also be used as a fragrance support. For example, an IFO gel (for example, a polyamide gel) is one suitable example of a gellant that may be used in embodiments of the invention to replace all or part of the polymer component.

A preferred shape of the reservoir is shown in the figures. This may generally be described as half of a ribbed disk. This shape permits air flow while still allowing the maximum heat distribution and optimal fragrance release.

Fragrances

One or more fragrances or odor neutralizers may be used in embodiments of the invention. If addition of fragrance is desired, suitable fragrances may be selected from those compiled by the U.S. Food and Drug Administration in Title 21 of the Code of Federal Regulations, Sections 172.510 and 172.515, incorporated by reference herein. Fragrance components selected from benzaldehydes, phenols, cinnamic aldehydes and esters, octadienes, dienes, cyclohexadienes, and terpenes may be used in the invention. Fragrance oils are also suitable for use alone or in combination with other fragrance chemicals. Suitable fragrance oils are, for example spice oil, flower oil, and fruit oil.

Other suitable fragrances include but are not limited to benzyl alcohol, ethyl maltol, furaneol, 1-hexanol, cis-3-hexen-1-ol, menthol, benzaldehyde, hexanal, cinnamaldehyde, citral, cis-3-hexenal, furfural, neral, vanillin, ethyl acetate, ethyl butanoate, ethyl decanoate, ethyl hexanoate, ethyl octanoate, hexyl acetate, isoamyl acetate, methyl butanoate, methyl salicylate, pentyl butanoate, pentyl pentanoate, sotolon, strawberry aldehyde, fructone, anethole, anisole, eugenol, dihydrojasmone, 2-acetyl-1-pyrroline, 6-acetyl-2,3,4,5-tetrahydropyridine, gamma-decalactone, gamma-nonalactone, delta-octalactone, jasmine lactone, massoia lactone, camphor, citronellol, linalool, nerol, nerolidol, alpha-terpineol, thujone, and thymol.

In further embodiments of the invention, fragrances and/or odor neutralizers are mixed with one or more hindered amines. The hindered amines useful in the instant invention are well known in the art and are described in detail in U.S. Pat. No. 6,221,115, the relevant parts of which are incorporated herein by reference. Examples of the hindered amines are: 1-(2-hydroxy-2-methylpropoxy)-4-octadecanoyloxy-2, 2,6,6-tetramethylpiperidine; 1-(2-hydroxy-2-methylpropoxy)-4-hydroxy-2,2,6,6-tetramethylpiperidine; bis(1-octyloxy-2,2,6,6-tetramethylpiperidin-4-yl)sebacate; bis(1-cyclohexyloxy-2,2,6,6-tetramethylpiperidin-4-yl)sebacate; 1-cyclohexyloxy-2,2,6,6-tetramethyl-4-octadecylaminopiperidine; 2,4-bis[(1-cyclohexyloxy-2,2,6,6-tetramethylpiperidin-4-yl)butylamino]-6-(2-hydroxyethylamino-s-triazine; bis(1-cyclohexyloxy-2,2,6,6-tetramethylpiperidin-4-yl)adipate; 1-(2-hydroxy-2-methylpropoxy)-4-oxo-2,2,6,6-tetramethylpiperidine; bis(1-(2-hydroxy-2-methylpropoxy)-2,2,6, 6-tetramethylpiperidin-4-yl)sebacate; bis(1-(2-hydroxy-2-methylpropoxy)-2,2,6,6-tetramethylpiperidin-4-yl)adipate; bis(1-(2-hydroxy-2-methylpropoxy)-2,2,6,6-tetramethylpiperidin-4-yl)succinate; bis(1-(2-hydroxy-2-methylpropoxy)-2,2,6,6-tetramethylpiperidin-4-yl)glutarate; and 2,4-bis{N-[1-(2-hydroxy-2-methylpropoxy)-2,2,6,6-tetramethylpiperidin-4-yl]-N-butylamino}-6-(2-hydroxyethylamino)-s-triazine) 1-methoxy-4-hydroxy-2,2, 6,6-tetramethylpiperidine; 1-methoxy-4-hydroxy-2,2,6,6-tetramethylpiperidine; 1-octyloxy-4-hydroxy-2,2,6,6-tetramethylpiperidine; 1-cyclohexyloxy-4-hydroxy-2,2,6,6-tetramethylpiperidine; 1-methoxy-4-oxo-2,2,6,6-tetramethylpiperidine; 1-octyloxy-4-oxo-2,2,6,6-tetramethylpiperidine; and 1-cyclohexyloxy-4-oxo-2,2,6,6-tetramethylpiperidine, or a mixture thereof.

In yet further embodiments of the invention, fragrances and/or odor neutralizers include one or more antioxidants. Antioxidants used in embodiments of the invention may be, for example, tertiary butylhydroquinone, n-octadecyl-3,5-di-tert-butyl-4-hydroxyhydrocinnamate, butylated hydroxyanisole, phenol bisphosphite, butylated hydroxytoluene, and phosphite compounds. An effective amount of antioxidant in the instant composition is 0.015% to 2.5% by weight of the EVA or other polymer, preferably 0.1 to 0.75% by weight and most preferably 0.2 to 0.5% by weight. In preferred embodiments of the invention, high concentrations of antioxidants are mixed with fragrance priori to addition of the fragrance/antioxidant mixture to any other components of the mixture.

Still further embodiments of the invention contemplate inclusion of the fragrance and/or odor neutralizer in a diluent prior to incorporation into a polymeric carrier. A diluent is organic, for example: triethyl citrate; di-isopropropyl adipate; di-octyl adipate; isopropyl myristate; isopropyl palmitate; butyl stearate; benzyl alcohol; benzyl benzoate; and diethyl pthalate. The quantity of diluent preferred is the quantity necessary for dissolving the fragrance or the antioxidant.

In one preferred embodiment, a selected fragrance and/or an odor neutralizer (with or without the other additives reported above) is embedded in and/or adsorbed on the polymer. Further information regarding creation of a fragrance/antioxidant/diluent mixture may be found in U.S. Pat. No. 7,220,288, which is incorporated by reference as if fully rewritten herein.

Dispensers

In a preferred embodiment, the invention includes an economical electric dispenser for controlling the release of volatile materials within a contained environment. The dispenser may be, for example, a two-piece disposable unit or a three-piece refillable unit as shown in the attached Figures.

The polymer fragrance reservoir is either molded on the heating element or is molded as a snap-on piece. Such construction encourages child safety. During operation of the air freshener, current flows through a resistor, causing the creation of heat that raises the temperature of the polymer and releases fragrance from the polymer.

Various resistors may be suitable for use in the invention. For example, it is expected that resistors of 5 KOhm, 8 KOhm, and 10 KOhm may be useful in certain embodiments of the invention. The dispenser may be modified to allow the resistor to have direct contact with or direct communication with the polymer support, for example by adding holes to the surface of the dispenser between the resistor and the dispenser, or by adding holes to the sides of the portion of the dispenser including the resistor.

Metal Inclusions

Metal inclusions may be added as a powder or as metal-coated beads of glass or ceramic. These inclusions are thought to alleviate the insulative properties of the fragrance support. It is believed that the metal prevents trapping of heat within the confines of the fragrance support.

Metal inclusion amounts may vary. For example, they may range between 0.5% to 2.0%, 0.5% to 1.0%, 0.1% to 0.5% and 0.2% to 0.3% of the total fragrance support composition by weight, including the fragrance and other additives.

Metal inclusion sizes may vary. For example, they may be powders. One preferred powder size is 325 mesh. Powders may range in size, for example, between 200 mesh to 400 mesh. They may also be flakes or strands. Metal strands may be up to 0.06 inches in length and 0.0125 inches in width. Flakes may be up to 0.04 inches in diameter.

Other Additives

Various other additives such as color additives may be added in different embodiments depending on desired characteristics of a particular fragrance dispenser.

Plasticizers may also be added to polymeric materials that are used in embodiments of the invention. These may include, for example, diethyl phthalate and triacetic acid ester of glycerin.

EXAMPLES

The following examples are given to help those skilled in the art appreciate the invention. They should not be construed to limit the scope of the claims.

Example 1

Example 1 describes the construction of a polymer support containing metal inclusions and a fragrance. An amount of fragrance that is 33.4% by weight of the anticipated final formula amount is weighed and loaded into a vessel. Into the fragrance is added antioxidant and hindered amine at 0.7% and 0.7% by weight of the anticipated final formula amount, respectively. An amount of 0.2% of a color solution is added. This is mixed until dissolution.

The fragrance solution is transferred to a 5 gallon drum. EVA in the amount of 65% by weight of the anticipated final formula amount is added as solid beads. Aluminum powder, if desired, is added at 0.3% by weight of the anticipated final formula amount. The drum is sealed and rotated until the fragrance mixture is completely absorbed into the EVA and the aluminum (if present) coats the beads.

The beads are loaded into an injection molding machine. It is preferred that prior to injection molding the beads be no larger than 325 mesh. A fragrance support is created in the desired shape through the injection molding process. Through operation of the injection molding process, the aluminum is distributed within the structure. The finished fragrance support may be packaged for sale as a refill item or may be placed within a housing (of plastic or other material) that includes a resistor and is constructed by means known to those of skill in the packaging arts.

I claim:

1. A fragrance distribution device, comprising:
 a housing;
 a resistor connected to said housing and capable of generating heat to be transferred to said housing;
 a fragrance support contained within said housing, said fragrance support comprising a thermoplastic carrier, at least one fragrance, and a plurality of metal inclusions distributed throughout the thermoplastic carrier wherein said metal inclusions are powders that have a size ranging between 200 mesh to 400 mesh.

2. The fragrance distribution device of claim 1, wherein said thermoplastic carrier is selected from the group consisting of ethylene vinyl acetate (EVA), ethyl vinyl alcohol, high density polyethylene, low density polyethylene, polystyrene, acrylic polymers, polycarbonates, polyurethanes, nylons, and mixtures and copolymers of the foregoing.

3. The fragrance distribution device of claim 2, wherein said thermoplastic carrier is EVA.

4. The fragrance distribution device of claim 1, wherein said metal inclusions are selected from the group consisting of aluminum, nickel, gold, silver, copper, platinum, and mixtures thereof.

5. The fragrance distribution device of claim 4, wherein said metal inclusions are aluminum.

6. The fragrance distribution device of claim 1, wherein said metal inclusions are present in an amount between 0.1 to 2.0% of the fragrance support by weight.

7. The fragrance distribution device of claim 6, wherein said metal inclusions are present in the amount of 0.1 to 0.5% by weight of the fragrance support.

8. The fragrance distribution device of claim 1, wherein said metal inclusions are powders that have a size of about 325 mesh.

9. The fragrance distribution device of claim 1, wherein said fragrance is selected from the group consisting of benzyl alcohol, ethyl maltol, furaneol, 1-hexanol, cis-3-hexen-1-ol, menthol, benzaldehyde, hexanal, cinnamaldehyde, citral, cis-3-hexenal, furfural, neral, vanillin, ethyl acetate, ethyl butanoate, ethyl decanoate, spice oil, flower oil, fruit oil, ethyl hexanoate, ethyl octanoate, hexyl acetate, isoamyl acetate, methyl butanoate, methyl salicylate, pentyl butanoate, pentyl pentanoate, sotolon, strawberry aldehyde, fructone, anethole, anisole, eugenol, dihydrojasmone, 2-acetyl-1-pyrroline, 6-acetyl-2,3,4,5-tetrahydropyridine, gamma-decalactone, gamma-nonalactone, delta-octalactone, jasmine lactone, massoia lactone, camphor, citronellol, linalool, nerol, nerolidol, alpha-terpineol, thujone, and thymol.

10. The fragrance distribution device of claim 1, wherein said metal inclusions are aluminum powder and said thermoplastic carrier is EVA.

11. The fragrance distribution device of claim 1, wherein said fragrance support comprises a recess, and wherein a part of said resistor is shaped to fit snugly within said recess, said recess providing an increased surface area for contact and ventilation of the fragrance support and resistor relative to a flat fragrance support abutting a flat resistor.

12. The fragrance distribution device of claim 11, wherein said recess is a half-cylinder.

* * * * *